(12) United States Patent
Gardon-Mollard

(10) Patent No.: US 6,523,729 B1
(45) Date of Patent: Feb. 25, 2003

(54) METHOD AND DEVICE FOR PULLING ON A LIMB A TUBULAR COMPRESSIVE ORTHOTIC DEVICE SUCH AS A STOCKING, TIGHTS OR SOCK MADE OF KNITTED ELASTIC TEXTILE MATERIAL

(75) Inventor: Christian Gardon-Mollard, Chamalieres (FR)

(73) Assignee: Innothera Topic International-Societe Annoyme, Arcueil (FR)

( * ) Notice: Subject to any disclaimer, the term of this patent is extended or adjusted under 35 U.S.C. 154(b) by 0 days.

(21) Appl. No.: 09/622,907

(22) PCT Filed: Mar. 2, 1999

(86) PCT No.: PCT/FR99/00454
§ 371 (c)(1),
(2), (4) Date: Dec. 22, 2000

(87) PCT Pub. No.: WO99/44558
PCT Pub. Date: Sep. 10, 1999

(30) Foreign Application Priority Data

Mar. 2, 1998 (FR) ............................................. 98 02487

(51) Int. Cl.[7] .............................................. A47G 25/40
(52) U.S. Cl. .................................................. 223/112
(58) Field of Search ............................ 223/111–1, 120

(56) References Cited

U.S. PATENT DOCUMENTS 5,031,806 A  7/1991  Alpert
5,601,220 A * 2/1997 Vossen ........................ 223/112
5,673,826 A * 10/1997 Stolk ........................... 223/112
5,924,609 A * 7/1999 Stolk et al. ................. 223/112
6,032,839 A * 3/2000 Joosten et al. .............. 223/112

FOREIGN PATENT DOCUMENTS

| DE | 4312603 A1 | * 10/1994 | ................. 223/112 |
| FR | 788477 | * 10/1935 | ................. 223/112 |
| FR | 2 340 708 A | 9/1977 | |
| FR | 2 647 008 | 11/1990 | |
| GB | 2 173 390 A | 10/1986 | |
| SE | 447 539 B | 10/1986 | |

* cited by examiner

Primary Examiner—Bibhu Mohanty
(74) Attorney, Agent, or Firm—Jacobson Holman PLLC

(57) ABSTRACT

The method comprises the following steps:

a) enveloping the limb (22), over a length corresponding at least to the length of the orthosis (18), in a flexible sleeve (10) of material having a low coefficient of friction and great strength in traction and resistance to tearing, the limb possibly having dressings or bandages present thereon;

b) the orthosis is put on over that portion of the limb which is enveloped by the sleeve, with this being performed manually, causing the orthosis to slide over its entire length on the sleeve interposed between the orthosis and the limb; and c) once the orthosis has been put on and put into place, the interposed sleeve is extracted by traction, the sleeve sliding between the orthosis and the limb which then come mutually into contact as the sleeve is extracted.

3 Claims, 3 Drawing Sheets

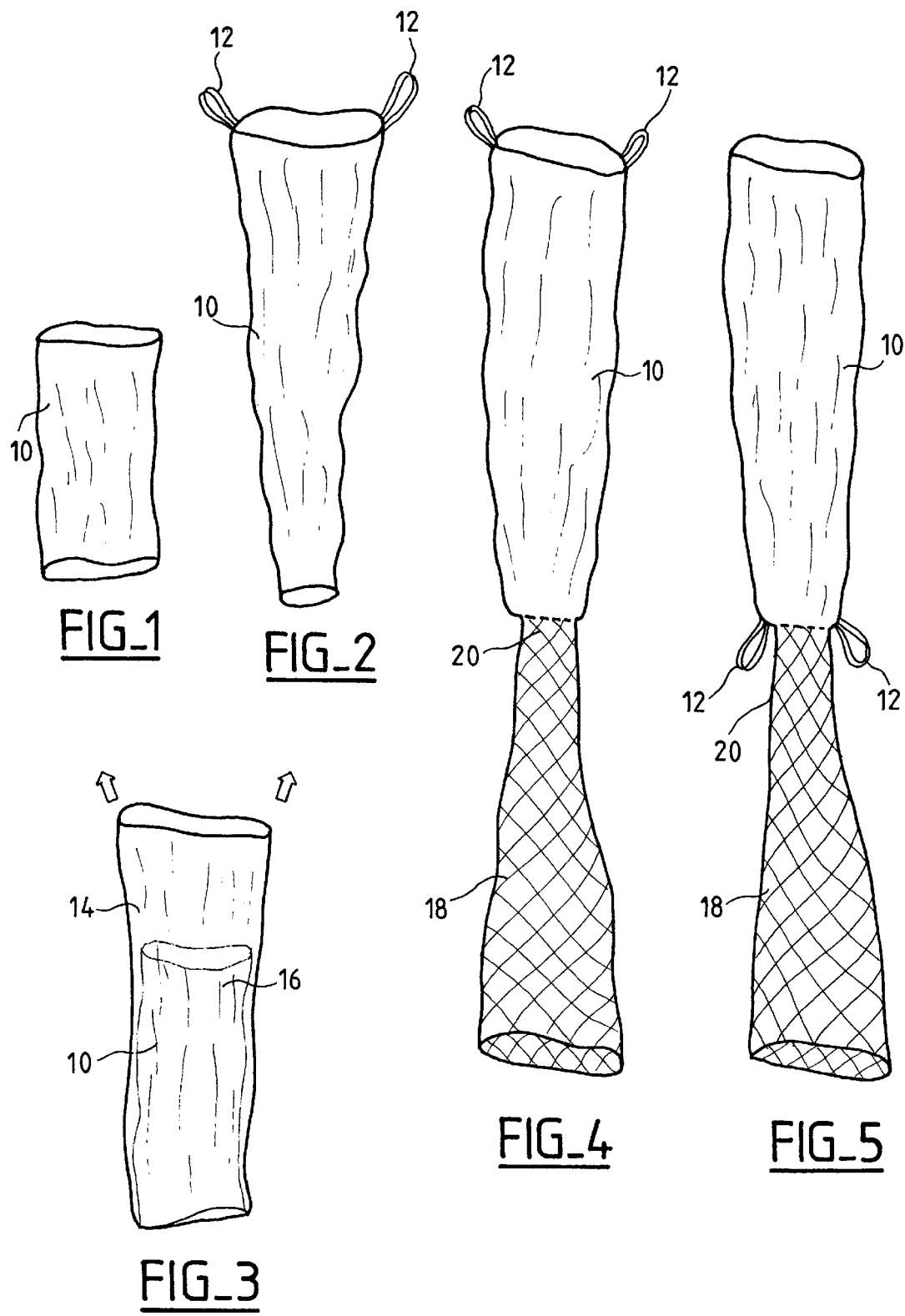

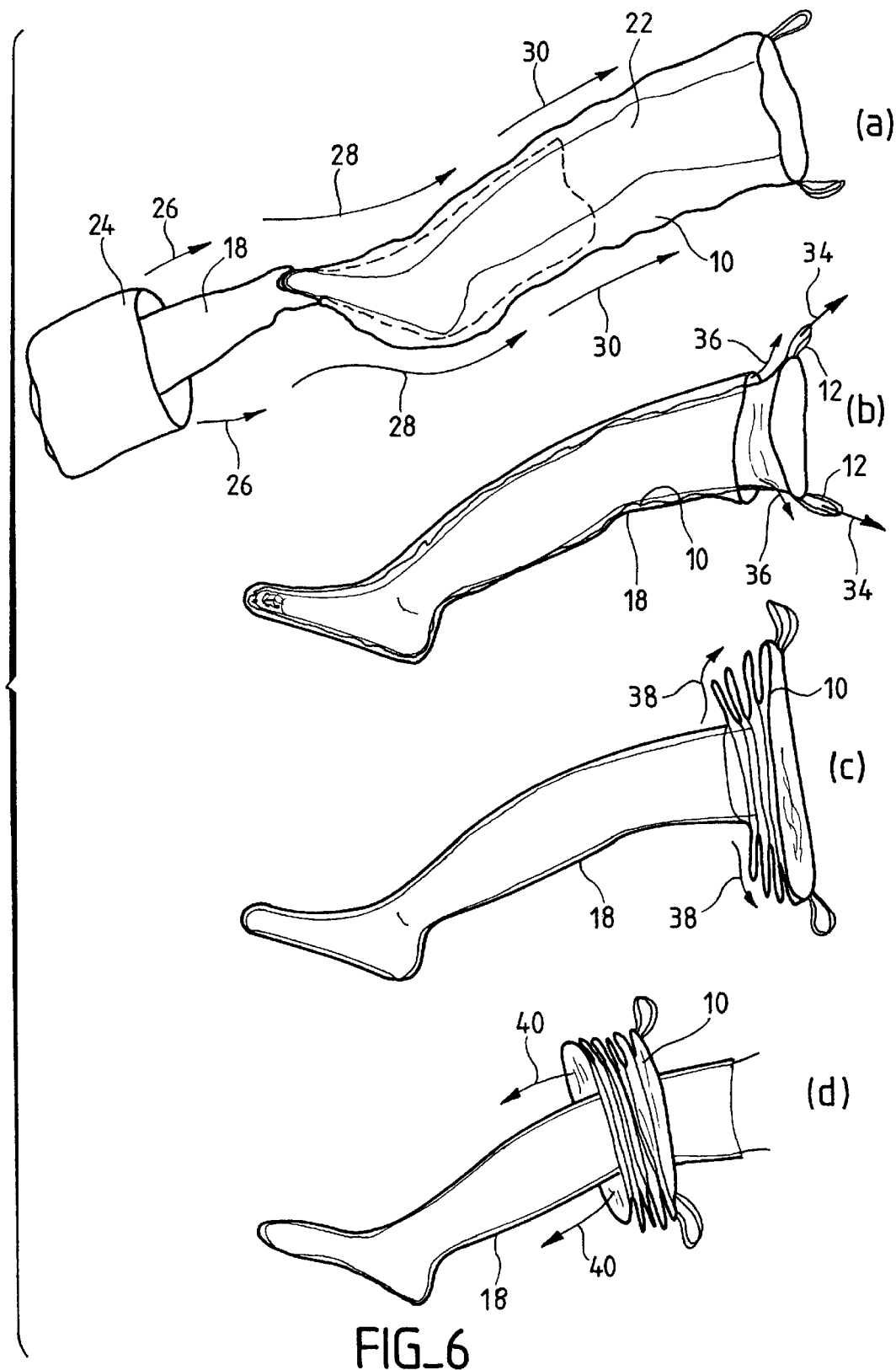
FIG_6

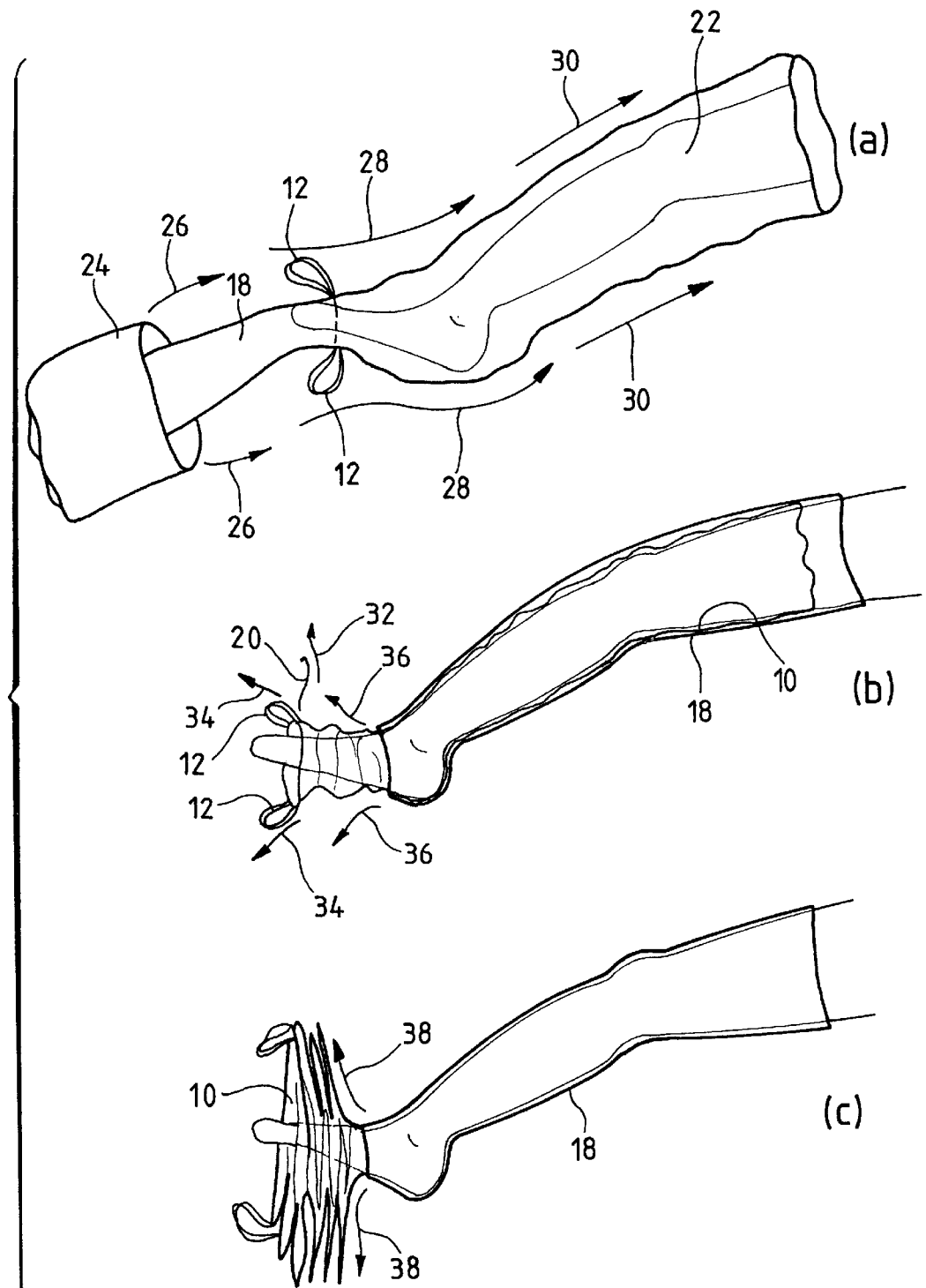
FIG_7

METHOD AND DEVICE FOR PULLING ON A LIMB A TUBULAR COMPRESSIVE ORTHOTIC DEVICE SUCH AS A STOCKING, TIGHTS OR SOCK MADE OF KNITTED ELASTIC TEXTILE MATERIAL

This is a 371 of PCT/FR99/00454 filed Mar. 2, 1999.

The invention relates to the field of tubular compressive orthoses made of a knitted elastic textile material, i.e. of the "elasticated stocking" type.

In the meaning of the present invention, such orthoses can have various shapes. For example, compressive orthoses for one or both lower limbs can be in the form of a stocking proper (covering the thigh and the calf), of tights (covering both lower limbs and the abdomen up to the waist, in a single piece), one-legged tights (tights provided with one leg only, for applying compression to only one of the lower limbs), or indeed socks (covering only the calf).

The invention also applies to compressive orthoses for the upper limbs.

The invention is therefore not limited to a particular article, but relates to all kinds of tubular compressive orthosis (i.e. excluding bandages) such as those described above.

To enable high compression to be applied to the limb(s), such orthoses are made of an elastic material, typically a knit of very tight texture, thereby giving rise to various difficulties.

In particular with orthoses of the stocking or tights type, one of the difficulties lies in putting it on over the foot and the ankle (where the orthosis is most difficult to put on and where compression at its strongest), with the risk of the orthosis being badly placed, particularly at the instep and the heel, which are zones where it is always rather difficult to put on an orthosis, particularly with increasing orthosis pressure.

This difficulty in putting on an orthosis is generally made worse by the fact that such orthoses are prescribed for treating circulatory diseases which often affect patients who are elderly, clumsy, sometimes suffering from a motor handicap, and suffering from arthritic phenomena that deform the hands and the feet, etc., i.e. people whose mobility is generally rather limited.

Furthermore, with post-surgical indications, after vein surgery, an orthosis can be made more difficult to put on by the dressings present on the leg after surgery, which dressings are often of the "American dressing" type, i.e. very absorbent and therefore very thick, thus getting in the way of putting on an orthosis even though it is essential to avoid moving them. An orthosis can also be difficult to put on because the patient being under general anesthetic, so the patient cannot contract muscles voluntarily to provide active resistance while the orthosis is being put on; under such circumstances, it is important to avoid forcing the passive joints of the patient.

This difficulty in putting on compressive orthoses is an obstacle that is known both to patients and to carers, and numerous types of device have been proposed for making it easier, generally when the orthosis is a stocking, and most such devices comprise metal and/or rigid structures that are complex to operate.

FR-A-2 340 708 describes one such device, in the form of a rigid Turkish slipper cut open at the toes; that accessory does indeed make it easier to pass the stocking over the foot, but it provides no help of any kind with putting it on over the remainder of the limb, which operation remains very difficult when the limb carries dressings and the patient is immobilized under anesthetic.

An object of the invention is to propose a method and apparatus that are simple to use for putting an orthosis of the above-specified type onto a limb.

It will also be seen that the putting-on device of the invention is not expensive to make, which means that a discardable device can be provided for single use only, which is particularly advantageous for use with orthoses that are for treatment of a venous ulcer, since the device which might into contact with the wounds and the serosities could be a vector for germs if it were to be used with other patients. It will also be seen that in this particular indication, the single-use device can be integrated in the orthosis so as to make it easier to put on, and be detachable therefrom subsequently, thus enabling a carer to use a one-piece product that is suitable for putting on directly, and whose element that serves for putting-on purposes only can be separated and discarded after use.

More precisely, the method of the invention is characterized by the following steps: a) the limb is enveloped, over a length corresponding at least to the length of the orthosis, in a flexible sleeve of a material that presents a low coefficient of friction and high strength in traction and against tearing; b) the orthosis is put on over that portion of the limb which is enveloped by the sleeve, with this being performed manually, causing the orthosis to slide over its entire length on the sleeve interposed between the orthosis and the limb; and c) once the orthosis has been put on and put into place, the interposed sleeve is extracted by traction, the sleeve sliding between the orthosis and the limb which then come mutually into contact as the sleeve is extracted.

If the orthosis is open at both its distal and its proximal ends, then the sleeve is extracted via the distal opening by being pulled outwards in the region of this opening. If the orthosis is closed at its distal end and open at its proximal end, then the sleeve is extracted via the proximal end by being pulled outwards through said opening, and it is then withdrawn by passing the sleeve as extracted in this way around the limb, over the orthosis.

The invention also provides a device for implementing the method, the device being characterized by a flexible sleeve of material that presents a low coefficient of friction and high traction strength, and dimensioned in such a manner as to enable the limb to be enveloped over a length that corresponds at least to the length of the orthosis.

The flexible sleeve can be made of cloth, in particular a cloth that is coated in a material having a low coefficient of friction. It is advantageously tubular and open at at least one of its ends. It may optionally comprise two thicknesses of material turned inside out, one on the other, by invagination.

In a particular embodiment that is particularly adapted to single use, one of the ends of the sleeve is secured to the distal end of the orthosis via a separable link.

To make the sleeve easier to extract, it can be provided at one of its ends with at least one reinforcing element forming a strap or a handle for taking hold of and pulling.

Other characteristics and advantages of the invention will appear on reading the following description of various embodiments given with reference to the accompanying drawings.

FIGS. 1, 2, and 3 show three possible embodiments of a putting-on device of the invention.

FIGS. 4 and 5 show two possible variants of a putting-on device of the invention associated with an orthosis intended more particularly for treating venous ulcer pathologies.

FIGS. 6 and 7 show the successive steps in the method of the invention respectively with the device being withdrawn from the top and with the device being withdrawn from the bottom.

The putting-on device of the invention is constituted by a flexible and deformable sleeve which is formed in this example by a piece of cloth suitable for surrounding and containing the limb (leg or arm) that is to receive the orthosis, and covering it on all sides.

By way of example, the sleeve can be made as a single piece of cloth wound around the limb, however it is preferably made in the form of a tubular article, i.e. one of the sides of the piece of cloth is sewn to an opposite side thereof so as to define a closed outline having a sleeve opening into which the limb is inserted. This opening which corresponds to the proximal end of the limb after the sleeve has been put on, is referred to below as the "top end".

The sleeve is thus open at its top end; it can also be open at its bottom end so as to make it possible, optionally, to allow the distal end of the limb to project therethrough, or on the contrary it can be closed at said bottom end, in which case the sleeve is in the form of a sack or bag. It will be understood below from the description of how the method of the invention is implemented, that a sleeve having two open ends (the variant shown in the various figures) is applicable to putting on any type of orthosis, whereas a sleeve having a single open end is applicable only to putting on an orthosis of the "open-foot" type.

The shape of the sleeve (referenced 10 in the figures) can be approximately cylindrical as shown in FIG. 1 (for putting on stockings and socks, for example) or it can be elongate and slightly tapering (for putting on stockings or orthoses that go up above the knee), as shown in FIG. 2.

An accessory 12 is advantageously provided for being taken hold of and pulled, which accessory is in the form of a strap, handle, tag, loop, etc. so as to help the patient or the carer remove the putting-on device more easily after the orthosis has been put into place (see below).

The device is either a single piece, i.e. constituted by a single thickness of cloth, or else a double piece as shown in FIG. 3, i.e. made up of two thicknesses 14, 16 with one thickness of cloth being turned over onto itself or "invaginated" like the finger of a glove being taken off, thereby making it even easier to put the compressive orthosis into place and to remove the device.

The material from which the sleeve is made is a material having a low coefficient of friction and great resistance to breakage (in traction and in tearing).

The concepts of "low coefficient of friction" and "great resistance to traction and tearing" are relative and mean that the method as described below must be capable of being performed in satisfactory manner by hand without help from any additional accessory, and without displacing the orthosis once it has been put into position, and without tearing the device while it is being extracted.

The mechanical properties required for this purpose can vary as a function of the more or less compressive nature of the stitch of the orthosis (compressive classes III or IV requiring greater traction force, and thus material that is stronger), on the structure of the stitch and the material of the orthosis, since certain characteristics (e.g. covering, incorporated elastane fiber, or incorporated elasto-diene fiber) can have an effect on the coefficients of friction of the orthosis relative to the skin and relative to the device.

By way of example, a particularly suitable material is Stabilkote 4, which is a cloth used in particular in sail-making. This material is made by weaving 30 denier warp and weft threads of 6.6 nylon polyamide, by impregnation using a melamine resin, and by coating in polyurethane. Such a cloth weighs 42±2 grams per square meter ($g/m^2$); it is therefore very lightweight but nevertheless highly resistant to tearing; by being coated in polyurethane it is given a coefficient of friction that is very low relative to the skin, relative to the surface of dressings or bands, relative to the knit of a compressive orthosis, and relative to itself.

On reading the present description, it will be understood that the simplicity in the design and the use of the flexible sleeve of the invention are the result in particular of the cloth sliding over itself, i.e. that the tube can be invaginated over a certain length prior to being placed on the leg that is to receive the orthosis. This manipulation can further be simplified for the user by means of a system of different colors (e.g. red to be put inside blue).

The size of the device must include a diameter that is large enough to enable it to be put onto the limb, typically a leg, which, in association with venous ulcer disease, can present one or more ulcers on which compresses or American dressings have been placed for medical purposes. This dimension can be at least 25 cm to 30 cm minimum diameter to cover all of the usual situations, assuming that the device is cylindrical in shape; if the device is conical in shape, then its dimensions are adapted to various sizes of calf, and of thigh if the device is to go above the knee.

It does not matter if the device is oversized, particularly if it needs to accommodate the thickness of any dressings that might be present on the limb. Such excess size will give rise to folds being formed in the device while the orthosis being put into place, however, as will be understood from the following detailed description of the method, these folds are far from harmful, since the coefficient of friction of the material of the device when rubbing against itself is very low, thereby making it even easier to extract.

In particular, such overdimensioning can make it easier to invaginate the distal end of the device, with, for example, the bottom (distal) third thereof being invaginated over the middle third, while the top (proximal) third serves essentially to exert traction for removing the device as a whole.

With certain diseases, such as ulceration of the legs, generally giving rise to large amounts of infection and trophic lesions, the device must be for single use only, i.e. discardable. Given its very low cost, both in material and in manufacture, such single use is entirely realistic.

Under such circumstances, the device can advantageously be secured to the orthosis as shown in FIGS. 4 and 5. In these figures, reference 18 designates an orthosis, in particular a discardable orthosis for compressing the leg following a venous ulcer, of the kind described in WO-A-97/47262 (Innothéra Topic International), to which reference can be made for further details. The single or double attached device 10 is sewn at 20 to the bottom end (distal end adjacent to the foot) of the orthosis 18 using a broad overcast stitch or a thread that can be cut, and at a sufficient distance from the toe to make it possible to detach the device after the orthosis has been put into place merely by cutting the stitches. Other methods of connection, e.g. high frequency welding, could naturally be envisaged providing they make it easy for the orthosis and the device to be separated once the orthosis has been put on.

Furthermore, for a universal article that can be used with any type of compressive orthosis (thigh-stocking, socks, tights), with open or closed foot portions, the device can be made "openable" at one of its end by various means such as fastener straps, adhesive, press-fasteners, laces, zip fasteners, etc.

Various embodiments of the device are possible, depending on whether it is desired to remove the device from the top (the loops 12 are then situated on its proximal end, as shown in FIG. 4), or from the bottom (the loops are then situated at its distal end, as in FIG. 5).

The various steps in the method of the invention for putting on an orthosis are described below with reference to FIGS. 6 and 7 which relate to two possible variants:

FIG. 6 relates to the case where the device, which is of the type shown in FIG. 2, is extracted from the top (proximal end), as must be the case with an orthosis of the kind shown which is in the form of a stocking that closes over the toes (this example is not limiting and the method can equally well be used for putting on any type of stocking, socks, tights, etc. whether open or closed at the foot or the ankle); in this variant the device is most advantageously invaginated initially as explained above, e.g. with the distal third invaginated in the middle third; and FIG. 7 shows the case of the device being withdrawn from the bottom (distal end) which implies that the orthosis must be open at its distal end, at the foot or the ankle; FIG. 7 relates to putting on an orthosis of the kind shown in FIG. 5 with an attached device, but this example is not limiting and the method is equally applicable to putting on any type of orthosis that is open at the foot or the ankle, with or without an attached device.

The first step, shown at (a) in FIGS. 6 and 7 consists in putting the device 10 into place on the limb 22, possibly with dressings thereon. In FIG. 7, where the orthosis 18 attached to the device, the orthosis is initially turned inside-out, i.e. with its inside face that is to be come into contact with the limb facing outwards.

The orthosis is then turned progressively the right way out (as at 24 in FIG. 7) and slid onto the leg (arrows 26, 28, 30), with this sliding being made easier by the very low coefficient of friction of the material of the device 22, so it is very easy for the patient or the carer to put on the orthosis using two hands, without it being necessary to use any particular accessory or to have help from a third person.

This leads to the situation shown in (b) in FIGS. 6 and 7, where the orthosis 18 is in place on the leg, with the device 10 being interposed between the leg and the orthosis.

When the orthosis is attached to the device as in FIG. 7, it is then necessary to cut or remove the thread 20 connecting the orthosis to the device (arrow 32) in order to separate these two elements.

The following step, shown at (b) and (c) in FIGS. 6 and 7 consists in extracting the device 10 by pulling on one of its ends, either its proximal end (extraction via the top, FIG. 6, with this extraction being made much easier by the device being invaginated) or from the distal end if that is possible (extraction from the bottom, FIG. 7); this traction can be exerted in particular by pulling on the loops 12 (arrows 34).

Given the very low coefficient of friction of the device relative to the skin and also relative to the cloth of the orthosis, the device is easy to extract completely (arrows 36, 38). However, because of its high coefficient of friction on the skin, and because of the constriction force due to the elasticity of the knit, the orthosis 18 does not move relative to the limb during this operation of extracting the device, and it therefore retains the position that was given to it on being put on.

In FIG. 6, where the device is extracted from the top, it is subsequently removed from the leg by being passed over the orthosis 18 as shown at (d) (arrow 40); naturally, to make this operation possible, the device must firstly be open at both ends, and secondly it must be of a diameter that is large enough to enable it to be passed over the top of the thigh.

What is claimed is:

1. A method of putting a tubular compressive orthosis (18) such as a stocking, tights, or a sock of knitted elastic textile material onto a limb, optionally with dressings or bandages present on the limb, the method being characterized by the following steps:

a) the limb is enveloped, over a length corresponding at least to the length of the orthosis, in a flexible sleeve (10) of a material that presents a low coefficient of friction and high strength in traction and against tearing;

b) the orthosis is put on over that portion of the limb which is enveloped by the sleeve, with this being performed manually, causing the orthosis to slide over its entire length on the sleeve interposed between the orthosis and the limb; and c) once the orthosis has been put on and put into place, the interposed sleeve is extracted by traction, the sleeve sliding between the orthosis and the limb which then come mutually into contact as the sleeve is extracted.

2. The method of claim 1 in which the orthosis is open at both its distal and its proximal end, the sleeve being extracted via the distal opening by being pulled out in the vicinity of said opening.

3. The method of claim 1 in which the orthosis is closed at its distal end and open at its proximal end, the sleeve being extracted via the proximal opening by pulling outwards in the vicinity of said opening, and then withdrawing the sleeve extracted in this way by causing it to pass around the limb, over the orthosis.

* * * * *